(12) United States Patent
Rosman et al.

(10) Patent No.: US 7,920,312 B2
(45) Date of Patent: Apr. 5, 2011

(54) OPTICAL FIBER SCANNING APPARATUS

(75) Inventors: Gavan Edmund Rosman, Camberwell (AU); Bradley Charles Jones, Endeavour Hills (AU); Robert Alan Pattie, Nyora (AU); Christopher Gerard Byrne, Berwick (AU)

(73) Assignee: Optiscan Pty Ltd. (AT)

( * ) Notice: Subject to any disclaimer, the term of this patent is extended or adjusted under 35 U.S.C. 154(b) by 431 days.

(21) Appl. No.: 11/855,001

(22) Filed: Sep. 13, 2007

(65) Prior Publication Data

US 2009/0015894 A1 Jan. 15, 2009

Related U.S. Application Data

(60) Provisional application No. 60/825,597, filed on Sep. 14, 2006.

(51) Int. Cl.
*G02B 26/08* (2006.01)

(52) U.S. Cl. ........................................ 359/199.1; 385/25

(58) Field of Classification Search .................. None
See application file for complete search history.

(56) References Cited

U.S. PATENT DOCUMENTS

| 6,294,775 B1 | 9/2001 | Seibel et al. |
| 6,845,190 B1 | 1/2005 | Smithwick et al. |
| 6,975,898 B2 | 12/2005 | Seibel |

FOREIGN PATENT DOCUMENTS

WO　WO 2004040267 A1 *　5/2004

* cited by examiner

*Primary Examiner* — Stephone B Allen
*Assistant Examiner* — Jennifer L. Doak
(74) *Attorney, Agent, or Firm* — Knobbe Martens Olson & Bear LLP

(57) ABSTRACT

A scanning apparatus and method, the apparatus comprising a light transmitter, a mount for supporting the light transmitter located remotely from its exit tip, a drive for driving the light transmitter to vibrate resonantly in a first direction and to vibrate non-resonantly in a second direction orthogonal to the first direction, and a synchronizer for synchronizing vibration of the light transmitter in the first and second directions so that the exit tip of the light transmitter executes a scan pattern. The drive applies a driving force to the light transmitter between the mount and the exit tip.

24 Claims, 10 Drawing Sheets

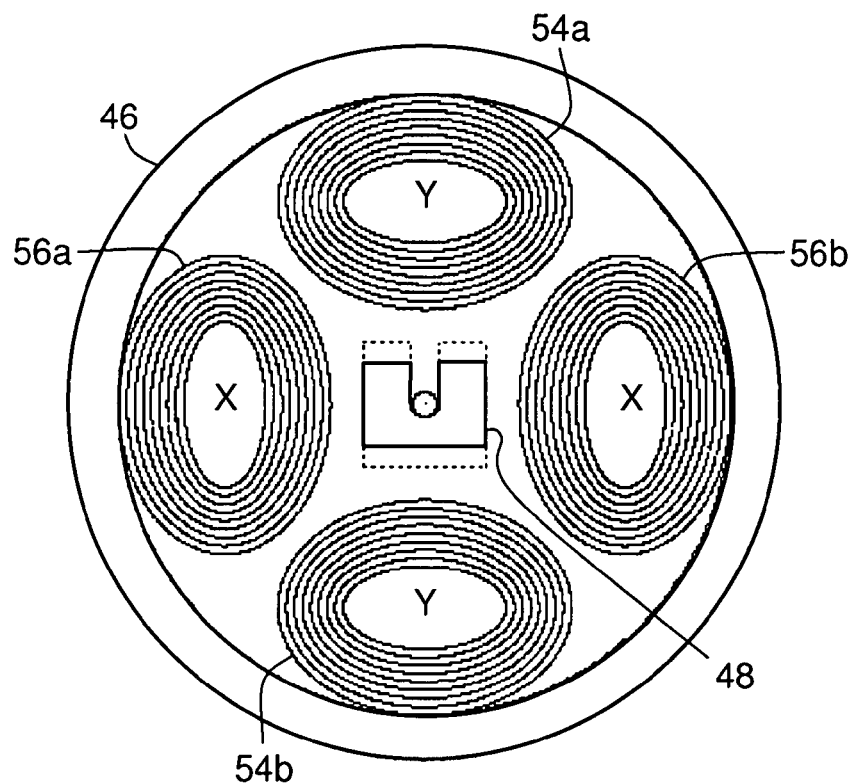
Figure 3
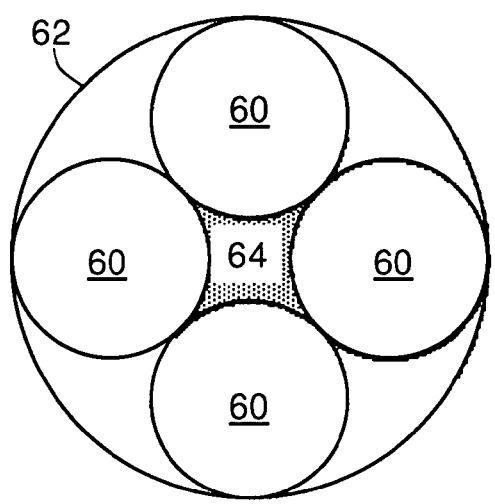 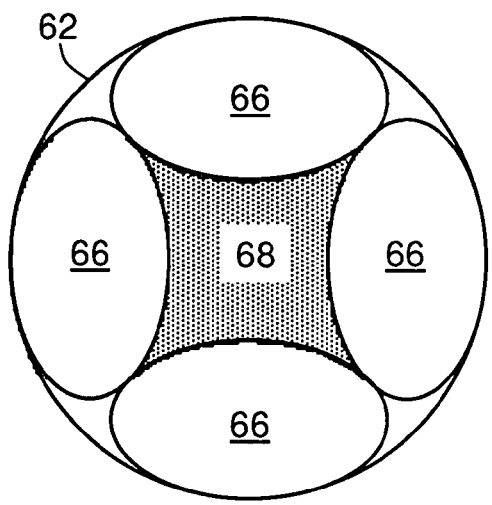
Figure 4A                    Figure 4B

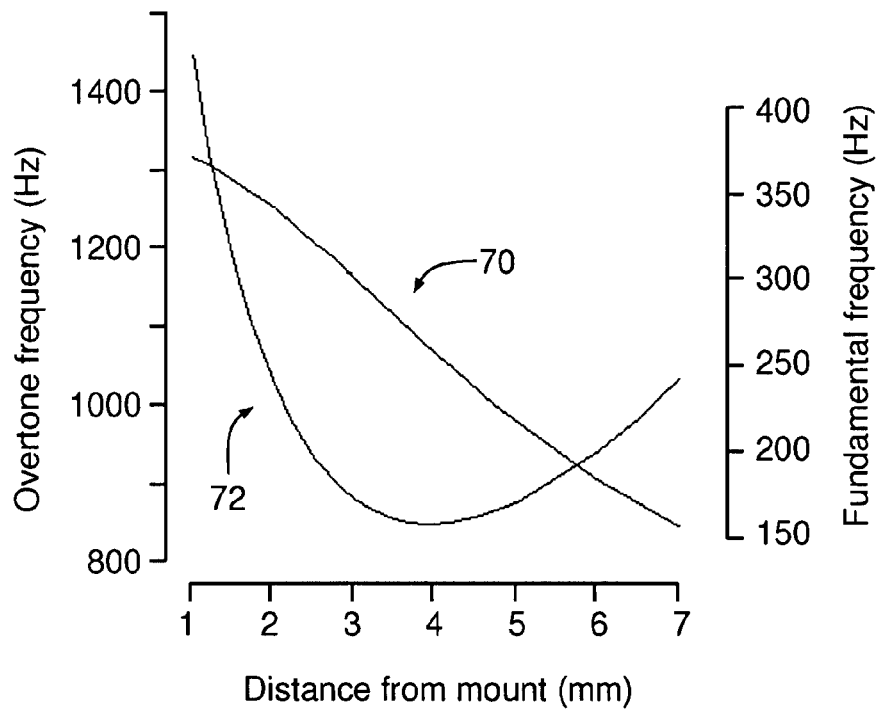
Figure 5
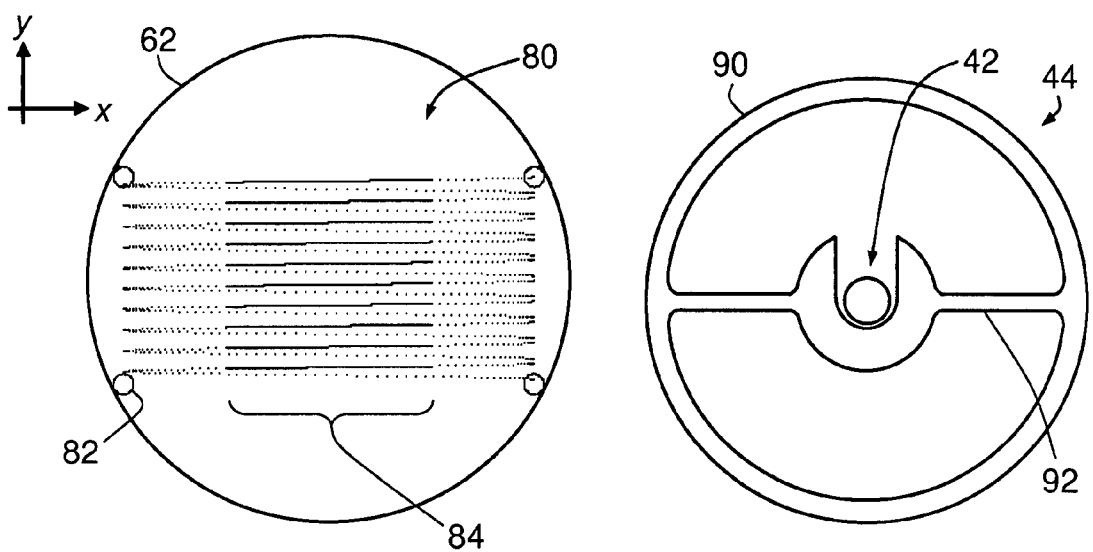
Figure 6
Figure 7

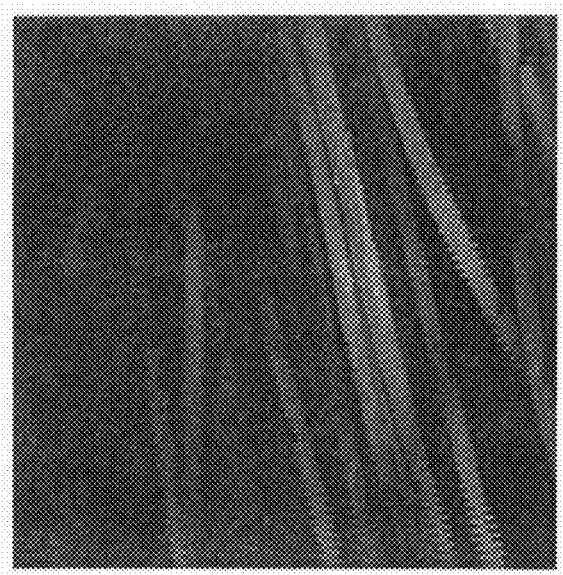 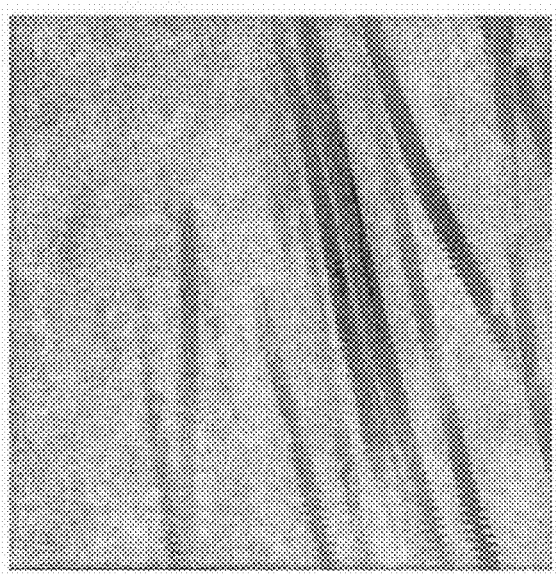
Figure 10A  Figure 10B
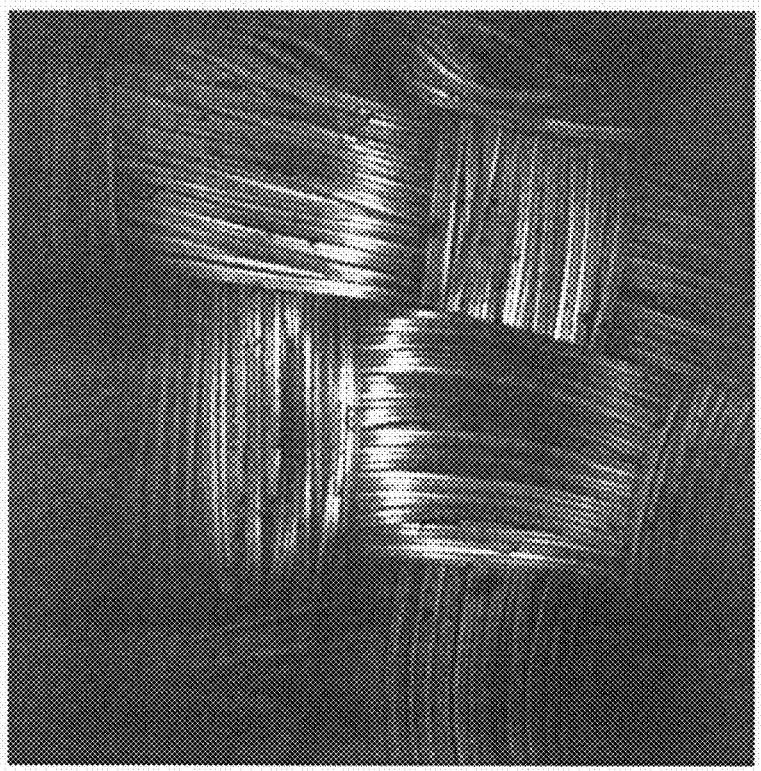
Figure 11

OPTICAL FIBER SCANNING APPARATUS

CROSS REFERENCE TO RELATED APPLICATION

This application claims the benefit of U.S. Provisional Patent Application No. 60/825,597 filed Sep. 14, 2006, the content of which is incorporated herein by reference in its entirety.

BACKGROUND OF THE INVENTION

1. Field of the Invention

The present invention relates to a method and apparatus for providing scanning with a light transmitter (such as an optical fiber), of particular but by no means exclusive application in microscopy, endoscopy (including endomicroscopy), and confocal microscopy and endoscopy.

2. Description of the Related Art

Some existing microscopes and endoscopes employ one or more optical fiber for light delivery to a sample and light collection from the sample. To image the sample, the delivered light is scanned across the sample; by scanning the exit tip of the fiber, this can been done by scanning the light after its emission by the fiber, or by providing multiple return fibers and collecting light sequentially from each.

The scanning of the fiber can be effected by attaching the exit tip of the fiber to a mechanical actuator, such as a vibrating tine of a tuning fork. Alternatively, one existing approach employs an actuator located at the base of a fiber, to impart a scanning motion to the fiber and hence its tip.

For example, four background art scanning mechanisms 10, 12, 14, 16 for use in small diameter endoscopes are shown in FIGS. 1A to 1D respectively. Scanning mechanisms 10 and 12 of FIGS. 1A and 1B each include an asymmetric fork 18 of ferromagnetic material to carry an optical fiber (not shown). A first (scanning) tine of fork 18 is axially located and a fixed X drive coil 20 surrounds both scanning tine and the second (balancing) tine. A Y scan is obtained by a see-saw action whereby the fork 18 rocks inside the X coil 20. The driving force for the Y scan is obtained with a permanent magnet 22 and an electromagnet 24 that carries a Y drive current. In scanning mechanism 12 of FIG. 1B, the magnetic circuit is folded to reduce overall length, and the Y coil 24 is hollow.

Synchronisation in both scanning mechanisms 10 and 12 is obtained with a piezo sensor mounted at the base of fork 18, which is used to drive the fork at resonance through an amplifier. The X scan in both mechanisms is sinusoidal, and usually the central half of the mechanical scan is used for imaging. The outer scan region, where the fiber tip slows down and reverses, is discarded.

Scanning mechanism 14 of FIG. 1C is the base excited cantilever using a tube piezo driver. This layout is seen in scanning microscopes, bar-code scanners, and a spiral scanning endoscope developed at the University of Washington. Such systems appear, however, to suffer from problems in the control of scan distortion.

Referring to FIG. 1D, scanning mechanism 16—disclosed in WO 04/40267—includes a slotted magnet 26 attached to a fiber 28 near the base 30 of the fiber, such that the fiber acts as a vibrating cantilever. The magnet 26 is activated and controlled by four electromagnets or coils 32 that surround the magnet.

Examples of some of these scanning systems are disclosed in U.S. Pat. No. 6,294,775, U.S. Pat. No. 6,975,898 and U.S. Pat. No. 6,845,190.

SUMMARY OF THE INVENTION

According to a first broad aspect, therefore, the invention provides a method of scanning with a light transmitter having an exit tip, comprising:

supporting the light transmitter in a mount located remotely from the exit tip;

applying a driving force to the light transmitter between the mount and the exit tip;

driving the light transmitter to vibrate resonantly in a first direction with a first driving force and to vibrate non-resonantly in a second direction orthogonal to the first direction with a second driving force; and synchronizing vibration of the light transmitter in the first direction with vibration of the light transmitter in the second direction so that the exit tip of the light transmitter executes a scan pattern.

The scan pattern may approximate a rectilinear raster scan, with the light transmitter executing sinusoidal vibration in the first direction and linear vibration in the second direction.

In one particular embodiment, the method includes vibrating the light transmitter in the first direction at the first overtone (also referred to as the second order of vibration) of mechanical resonance.

The method may include:

driving the light transmitter with an axially polarised magnet mounted on the light transmitter (such as near the mount), a first pair of axially oriented electromagnetic coils located on either side of the magnet in the first direction comprising a drive coil for driving the magnet in the first direction and a sensor coil for providing a signal for use in generating a position signal indicative of the position of the magnet in the first direction, and a second pair of axially oriented electromagnetic coils located on either side of the magnet in the second direction for driving the magnet in the second direction; and using the position signal to provide positive feedback to maintain light transmitter vibration in the first direction (and optionally for synchronising an image display).

In one embodiment, the method includes deriving the position signal by integrating the output signal of the sensor coil.

In a particular embodiment, the method may include subtracting a signal proportional to the drive current from the position signal to compensate for contamination of the position signal by a current induced in the sensor coil by the magnetic field of the drive coil.

In these embodiments, the magnet may be tapered in the second direction to maximize the volume of the magnet that can be accommodated between the second first pair of electromagnetic coils (owing to the rotation of the magnet as it is scanned in that direction). However, the magnet may be less tapered or untapered in the first direction (owing to the almost parallel motion of the magnet in the first direction when position at or near the antinode).

In other embodiments, additional coils may be employed for driving the light transmitter in the first direction, the second direction, or in both the first direction and second directions.

In one embodiment, the method includes locating the magnet substantially at a vibration antinode so that the magnet moves laterally without significant rotation, or substantially at a minimum in the overtone frequency versus magnet position curve to minimize required light transmitter length. In another embodiment, the method includes locating the magnet substantially at both a vibration antinode and a minimum in the overtone frequency versus magnet position curve.

For such magnet locations the resultant fundamental resonant frequency may be too low for the desired frequencies (such as require in some scanners), so it becomes desirable to employ an overtone resonance (e.g. the first overtone), such as at around four times the frequency.

The method may include vibrating the light transmitter in the second direction non-resonantly with low frequency alternating current excitation of the second pair of coils.

That is, the magnetic force available in some compact scanners may be limited, so the magnet may in some embodiments be removed from the mounting point of the light transmitter (or base) to obtain sufficient bending moment for tip desired deflection (particularly if driven in that direction with low frequency alternating current excitation and non-resonant operation).

In an alternative embodiment, the method includes vibrating the light transmitter in the second direction non-resonantly with varying direct current excitation of the second pair of coils. In such an embodiment, the method may include providing a restorative force (for restoring the light transmitter) with a spring or with the resilience of the light transmitter.

The light transmitter typically comprises an optical fiber, which may be single moded but need not be, according to application. Alternatively it may comprise a plurality of fibers or a fiber bundle, where each fiber may be single moded or otherwise.

The method may include providing negative feedback at the fundamental frequency in both first and second directions.

This would be done because a low fundamental resonance frequency creates a susceptibility to external vibrations, and any signals around this frequency in a linear drive.

The method may include mounting the light transmitter to have compliance in the first direction that is significantly different from compliance in the second direction.

The method may include mounting the light transmitter on a thin transverse beam. The predominantly torsional strain of this beam provides the additional compliance to lower the resonant frequency in one direction.

In another embodiment, the method includes mounting the light transmitter on a cantilever with a lower resonant frequency in one (e.g. y) direction than in the other (e.g. x) direction.

According to a second broad aspect, the invention provides a scanning apparatus, comprising:

a light transmitter having an exit tip;

a mount for supporting the light transmitter located remotely from the exit tip;

a drive for driving the light transmitter to vibrate resonantly in a first direction with a first driving force and to vibrate non-resonantly in a second direction orthogonal to the first direction with a second driving force; and a synchronizer for synchronizing vibration of the light transmitter in the first direction with vibration of the light transmitter in the second vibration so that the exit tip of the light transmitter executes a scan pattern;

wherein the drive applies a driving force to the light transmitter between the mount and the exit tip.

The apparatus may include a drive comprising:

an axially polarised magnet mounted on the light transmitter (such as near the mount);

a first pair of axially oriented electromagnetic coils located on either side of the magnet in the first direction comprising a drive coil for driving the magnet in the first direction and a sensor coil for providing a signal for use in generating a position signal indicative of the position of the magnet in the first direction; and a second pair of axially oriented electromagnetic coils located on either side of the magnet in the second direction for driving the magnet in the second direction;

wherein the position signal is suitable for providing feedback to maintain light transmitter vibration in the first direction (and optionally for synchronising an image display).

In one embodiment, the apparatus includes an integrator for integrating the output signal of the sensor coil to generate the position signal.

In a particular embodiment, the apparatus is configured to subtract a signal proportional to the drive current from the position signal to compensate for contamination of the position signal by a current induced in the sensor coil by the magnetic field of the drive coil.

In these embodiments, the magnet may be tapered in the second direction to maximize the volume of the magnet that can be accommodated between the second first pair of electromagnetic coils. However, the magnet may be less tapered or untapered in the first direction.

In one embodiment, the magnet is located substantially at a vibration antinode so that the magnet moves laterally without significant rotation, or substantially at a minimum in the overtone frequency versus magnet position curve, or substantially at both a vibration antinode and a minimum in the overtone frequency versus magnet position curve.

The apparatus may be configured to vibrate the light transmitter in the second direction non-resonantly with low frequency alternating current excitation of the second pair of coils.

In other embodiments, the apparatus includes a source of varying direct current for exciting the second pair of coils and thereby vibrate the light transmitter in the second direction non-resonantly. In such embodiments, a restorative force may be provided by the resilience of the light transmitter, or the apparatus may include a spring or other resilient mechanism for providing a restorative force.

The light transmitter typically comprises an optical fiber. Alternatively it may comprise a plurality of fibers or a fiber bundle.

The mount for the light transmitter (such as a thin transverse beam or a cantilever) may have significantly different compliances in said first and second directions.

The apparatus may include an imaging system for processing return light from the light transmitter and displaying an image generated therefrom.

The invention also provides an imaging apparatus comprising a scanning apparatus as described above, such as a microscope, an endoscope, an endomicroscope or an optical coherence tomograph.

In some embodiments the imaging apparatus is a confocal imaging apparatus, such as a confocal microscope or a confocal endoscope or a multiphoton endoscope.

BRIEF DESCRIPTION OF THE DRAWING

In order that the invention may be more clearly ascertained, embodiments will now be described, by way of example, with reference to the accompanying drawing, in which:

FIG. 3 is a cross-sectional schematic view of the coils of the scanner of FIG. 2A;

FIGS. 4A and 4B are schematic views illustrating the benefit of elliptical coils in the scanner of FIG. 2A compared to circular coils;

FIG. 5 are plots of the fundamental and first overtone frequencies for a total fiber length of 18 mm as functions of the distance of the magnet from the mount of the scanner of FIG. 2A;

FIG. 6 illustrates an example of a sine/sawtooth scan pattern employed by the scanner of FIG. 2A;

FIG. 7 is a schematic view of the mount of the scanner of FIG. 2A;

FIG. 10A is an exemplary image of fluorescent fibers collected with an endoscope including a scanner constructed according to an embodiment of the present invention;

FIG. 10B is a negative version of the image of FIG. 10A, provided for clarity;

FIG. 11 is an exemplary image of woven fibers collected with an endoscope including another scanner constructed according to an embodiment of the present invention;

DETAILED DESCRIPTION

Figure 2A:
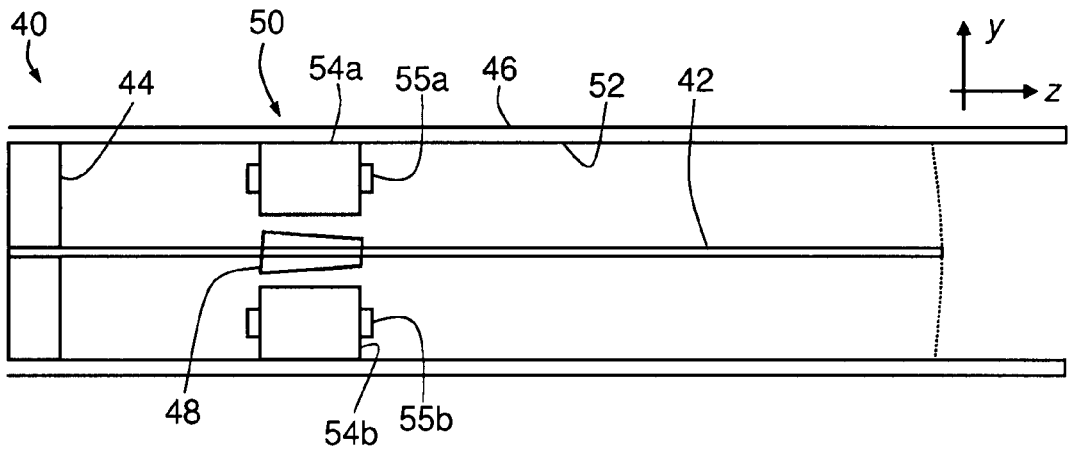
FIG. 2A is a schematic side view of a scanner according to a first embodiment of the present invention.

A scanner according to a first embodiment of the present invention is shown schematically at 40 in FIG. 2A, which is a cross sectional side view of the scanner. Scanner 40 is adapted for use as the scanning mechanism of an endoscope, and includes a flexible optical transmitter in the form of a standard optical fiber 42 mounted in a mount 44 and surrounded by a generally cylindrical housing 46. It should be noted that the flexible optical transmitter may alternatively be in the form of a fiber bundle, but in the following description, for simplicity, it will be referred to as "fiber 42" rather than as "fiber or fibers 42", though it should be understood that the latter may be appropriate in some embodiments.

The scanner 40 also includes a permanent magnet 48 mounted on fiber 42, at approximately a quarter of the length of the fiber from mount 44. The precise location of magnet 48 is discussed in detail below. The magnet can be mounted in any suitable way, including by locating the fiber in an aperture through the magnet or in a slot in one lateral face of the magnet; the magnet will typically be held in place with glue. In this embodiment magnet 48 has a slot (not shown) in its upper face, in which the fiber is located and held by glue.

The length of fiber 42 from mount 44 to magnet 48 is about 4 mm, and from mount to fiber tip 18 mm; the fiber 42 has a diameter of approximately 125 micron. The length of magnet 48 is about 2 mm. This geometry is suitable in view of the stiffness of a standard fiber of these dimensions. The distance of magnet 48 from mount 44 is greater than might be expected, but is employed to obtain the desired Y deflection without the benefit of mechanical Q. As a result the fundamental resonance frequency (of about 200 Hz) is relatively low and may not be suitable for imaging in some applications. This frequency also leads to sensitivity to unwelcome interference due to ringing in response to external vibrations. In addition, a fast Y retrace can induce long term ringing which carries over into a displayed image. The direct relationship between gravitational deflection and resonance frequency is discussed in more detail below.

The scanner 40 includes a drive in the form of four electromagnetic coils 50 located around magnet 48 spaced equally from each other, inside interior wall 52 of housing 46. The four coils comprise two Y coils 54a, 54b (shown in this figure) and two X coils (not shown) aligned in a plane perpendicular to the plane of the Y coils. Each coil has an elliptical cross section and is wound about a silicon steel or permalloy core (e.g. core 55a of coil 54a); each core has an elliptical cross section of ~0.8 mm major axis and ~0.4 mm minor axis, and in one particular embodiment a 0.7 mm major axis and a 0.3 mm minor axis. The coils abut the interior wall of cylindrical housing 46, and are supported by their cores; the cores are in turn attached to and supported by a frame (not shown)—to which the fiber mount 44 is also attached—around which the housing 46 is fitted.

As is explained in greater detail below, the fiber 42 is driven resonantly in the x direction (the 'fast scan') with an operating frequency of about 850 Hz, using the first overtone (automatically selected by the electronics). The orthogonal (i.e. y) direction is scanned in a non-resonant manner using a low frequency alternating current drive.

Though discussed in greater detail below, briefly, overtone operation in the x direction is obtained by using one X coil (referred to as the X drive coil) to produce the driving force, and the other X coil as a sensor (the X sensor coil). The emf induced in the X sensor coil is approximately proportional to the magnet velocity, and this induced voltage is electronically integrated to provide feedback information. There is also a directly induced voltage from the X drive coil. This is cancelled by sampling the drive current and subtracting a balancing proportion from the integrated waveform.

The signal proportional to the movement of the magnet 48 is used both for positive feedback after phase shifting to keep the fiber 42 vibrating, and also for synchronising an image display if—as would be usual—the output of scanner 40 is ultimately coupled to such a display. A frequency selective filter is included in the feedback path to prevent oscillation at the fundamental frequency of the cantilever. This arrangement is self-starting at the required overtone.

Y coils 54a, 54b provide vibration in the y direction; they provide balance and the required greater force needed for non-resonant scanning. The symmetry also reduces any direct induction into the X sensor coil, and the resonant drive signal into Y coils 54a, 54b.

Sensing of unwanted vibration at the fundamental in the y direction is accomplished with a bridge circuit. The emf induced by movement of the magnet 48 is separated and electronically enhanced by a frequency selective filter and used in a negative feedback loop. A monitor signal is also provided so that any mechanical disturbance can be detected, even while the scanner is in operation.

It should be noted that magnet 48 is generally trapezoidal in shape both in the plane depicted in FIG. 2A and—to a lesser degree—in the plane perpendicular thereto, such that it tapers away from mount 44. This maximizes the angle through which fiber 42 (and hence magnet 48) can be deflected—from the equilibrium position shown in this figure—both in the plane of the figure and in the plane perpendicular to that plane, as constrained by avoiding contact with the coils and maximizing the volume of the magnet.

Thus, the motion of the magnet is maximized for the space provided, which is important for use in a small diameter endoscope. Similarly, the coils 50 are designed to minimize their volume for their desired strength. FIG. 3 is a cross-sectional view of Y coils 54a, 54b and X coils 56a, 56b (within housing 46). All four coils are elliptical so that they impinge as little as possible on the space interior to the coils (in which the fiber 42 and magnet 48 must move) while maintaining the desired number of windings. The resulting ellipses each occupy one third of the housing diameter, leaving one third for the magnet 48 when in motion.

At maximum size the coils touch the housing 46 with equal curvature, and touch each other. The deflection of the magnet is calculated from elastic beam theory and the desired (or required) fiber tip deflection. The maximum magnet cross section that can be accommodated can then be determined. The benefit of using elliptical rather than circular coils is evident from FIGS. 4A and 4B. FIG. 4A depicts four circular coils 60 within a housing 62 (shown in cross-section), with a shaded interior space 64 left vacant for the fiber and magnet; such coils could be employed in scanner 40. FIG. 4B, however, depicts the preferred arrangement of this embodiment, with four elliptical coils 66; shaded interior space 68 for the motion of the fiber and magnet is approximately twice the width and height of the space 64 of FIG. 4A. The additional internal space allows either a larger magnet or greater beam deflection—or both—than would be possible with circular coils.

Housing 46—and hence scanner 40—has a final overall diameter of ~4.5 mm and length of ~30 mm. Indeed, a scanner according to this embodiment with a diameter of 3.5 mm has been constructed. In addition, a version with a diameter of 3.0 mm and a length of 23 mm has been designed, and it is envisaged that still smaller versions could readily be constructed.

Figure 2B:
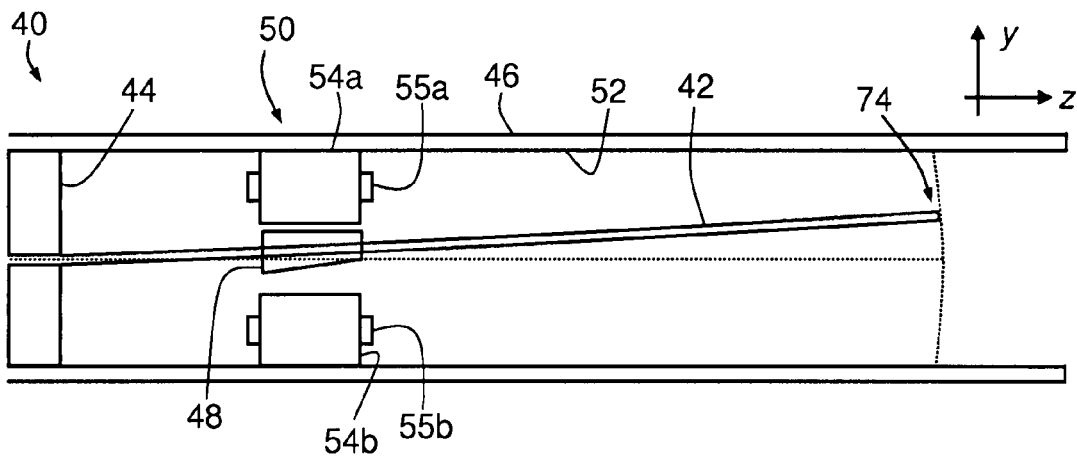
FIG. 2B is a schematic side view of the scanner of FIG. 2A in use.

FIG. 2B is a cross sectional side view of the scanner 40 at full Y deflection, that is, with fiber 42 deflected to its maximum extent in the Y direction. Scanner 40 is arranged to resonate at the first overtone in the X direction, however, as is illustrated schematically in FIG. 2C. A practical frequency range for mechanical resonant scanning is around 800 to 1000 Hz (or in some cases up to 1600 Hz) so, as mentioned above, scanner 40 is adapted to resonate at a first overtone of around 850 Hz. The permanent magnet 48 is located close to the antinode for this mode, so the magnet does not move far (despite a greater tip deflection in the x direction than in the y direction) and, when moving, is not rotated relative to its rest alignment by as great an angle as is apparent in the Y scan shown in FIG. 2B. This has two consequences: little if any taper need be applied to the magnet 48 in the magnet's cross section that is apparent in FIG. 2C, and the size of that cross section can be maximized to take advantage to this minimal deflection.

The position of permanent magnet 48 along the fiber 42 is selected, in coarse terms, to provide sufficient scanning amplitude in the y direction (as the closer magnet 48 is to mount 44, the greater will be the scanning amplitude in the y direction), while providing adequate clearance in the x direction. This is then adjusted for optimum 1st overtone performance, and checked for compatibility with the requirement for low frequency alternating current Y deflection.

For a total fiber length of 18 mm the fundamental and first overtone frequencies have been computed and are plotted in FIG. 5 (as functions of the distance of the magnet 48 from the mount 44). The fundamental frequency 70 monotonically decreases as the distance of the magnet 48 from the mount 44. However, the overtone frequency 72 has a minimum at approximately 4 mm, which is in fact close to the position selected to provide a suitable Y deflection using a first overtone frequency of about 850 Hz. This position may be described as "optimum" in the sense that it employs the shortest fiber for this desired frequency, so minimizes the overall length of the scanner.

For a small diameter scanner (such as a long rigid scanner made to fit down a small diameter tube), where diameter is the over-riding consideration, the magnet would be positioned at the antinode to get parallel magnet motion and best clearance. However, if the scanner is for use in the rigid tip of a flexible endoscope (which are typically more useful if the rigid tip length is short), the aforementioned minimum frequency condition may be the preferred criterion, to provide the shortest scanner length for a given frequency of (overtone) operation. With practical clearances the magnet can be positioned between these two ideal positions; both are defined by parabolic minima so there would be very little sacrifice of performance. In this embodiment, magnet 48 is located at the minimum shown in FIG. 5, thus minimizing the length of the scanner, but this also places magnet 48 essentially at the vibration antinode so scanner diameter can also be minimized.

FIG. 6 illustrates a sine/sawtooth pattern 80, as employed with scanner 40. FIG. 6 is a cross sectional view through housing 62 at the position of the tip 82 of fiber 42. The tip 82 is shown in its four extreme deflections, with the tip 82 as close as possible to the housing 62 in each case to provide the largest possible image. Generally, only the central part 84 (shown with a solid curve) of the x direction sinusoidal deflection 80—and with tip 82 moving in one direction (such as left to right)—is used for data collection. However, the scanner 40 uses almost the entire vertical or y direction scan (which comprises essentially a linear sawtooth motion), amounting in practice to approximately half the x direction travel of the tip 82. This maintains an approximately square image. A greater portion of the x direction deflection may be used, if a greater degree of image distortion is acceptable or post-imaging processing is used to reduce that distortion.

Other scan patterns have been developed for those cases where the bimotional fiber cannot be sufficiently deflected except at resonance and advantage is taken of mechanical Q. This occurs when the available driving force is too small to deflect the fiber directly at low frequency when driven with an alternating current drive.

Figure 1A:
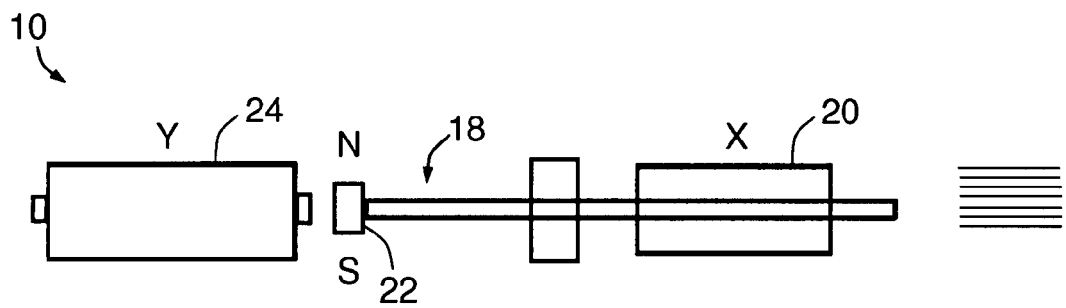
FIGS. 1A to 1D are schematic views of background art scanning mechanisms.
Figure 1B:
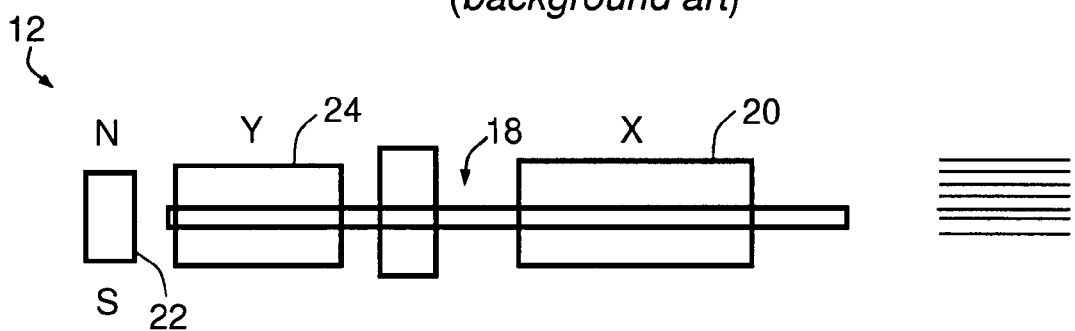
Figure 1C:
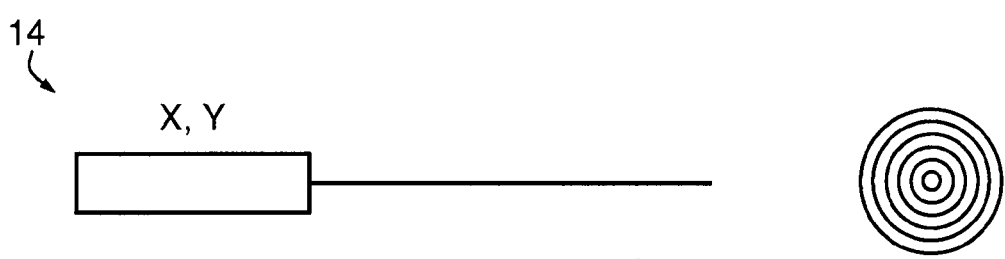
Figure 1D:
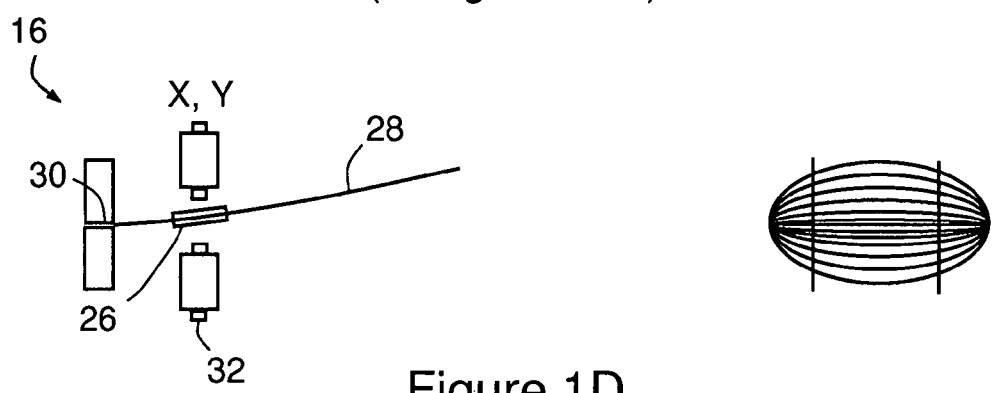

Another possible scan pattern for use with scanner 40 comprises a variable ellipse where the fiber touches the tube at only two points (i.e. the ends of the ellipse). In terms of speed, the area suitable for imaging when such a variable ellipse is used is slightly larger than with the pattern shown in FIG. 6. The Y amplitude of the elliptical pattern can be increased compared with that shown in FIG. 1D, but the mapping to a display then becomes more difficult; for some applications, however, those scan limits would be acceptable even with direct conversion to a rectilinear display.

A potential problem of scanner 40—as it comprises a bimotional resonant cantilever—is that of whirling. Mount 44 is designed to provide a compliance that differs in the x and y directions; essentially straight line scanning can then be obtained with magnet 48 acted on by a single driving coil. FIG. 7 is a schematic view of mount 44 (viewed along the z axis). Mount 44 includes a circular frame 90 with a thin transverse beam 92 that supports the base of the fiber 42. The transverse beam 92 can more readily twist to permit deflection in the y direction than it can warp to permit deflection in the x direction, so—as discussed above—compliance which is significantly different in the x and y directions.

Alternatively, a thin polymer strip (of, say, 0.1 mm thickness and 1 mm width) could be attached laterally to the fiber 42 in front of a substantially rigid mount. This would also provide significantly different compliance in the x and y directions.

Whatever technique is employed, it is estimated that the compliance is sufficiently different if the difference—expressed in terms of frequency difference—is about 20 Hz (provided that the permanent magnet 48, when scanning in the x direction, does not come too close to the pole pieces of the Y coils 54a, 54b. As a low frequency alternating current Y drive is employed, this frequency difference can be made quite large without endangering the operation of scanner 40 in the y direction.

X Electronics

The X electronics of scanner 40 control the resonant scanning in the x direction, by sensing the x position of the magnet 48, controlling deflection at the overtone (with a positive feedback loop), suppressing vibration at the fundamental (with a negative feedback loop), and provides image synchronisation.

X Position Sensing

Figure 8:
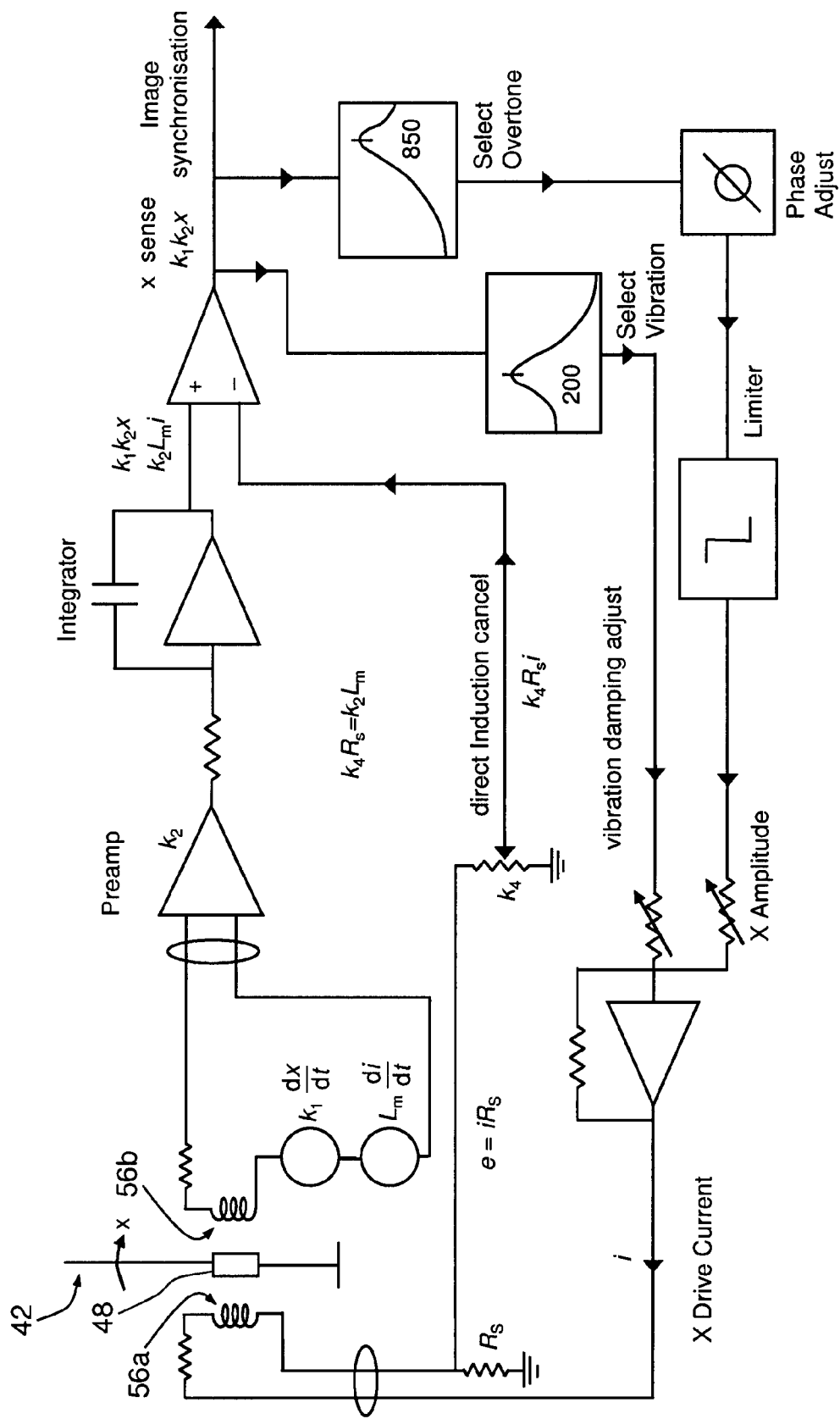
FIG. 8 is a circuit diagram of the X electronics of the scanner of FIG. 2A.

FIG. 8 is a circuit diagram of the X electronics, which also depicts fiber 42 and magnet 48 between X drive coil 56a and X sensor coil 56b. As magnet 48 moves between the X coils, an emf is induced in X sensor coil 56b that is proportional to magnet velocity (rather than position), owing to magnet's motion relative to X sensor coil 56b. There will also be significant direct induction from the magnetic field of the X drive coil 56a into the X sensor coil 56b. More precisely, the mutual inductance will result in a signal proportional to the derivative of the drive current. It is easily measured off resonance and can be quantified.

Both of these effects—the induced emf and the direct induction—are annotated in the figure as two voltage generators (respectively $$k_1 \frac{dx}{dt} \text{ and } L_m \frac{di}{dt})$$

in series at the back of the coil impedance. They pass (from the scanner 40) to a preamplifier and from there to an integrator. The output of the integrator is a position signal, but it is still contaminated by the direct induction, now proportional to the X drive current. This contaminant is removed by subtracting a portion of the drive current sampled as shown at the base of the X drive coil 56a. Finally, at the top right of the circuit diagram a signal is produced that is a good indicator of magnet position. There is a slight asymmetry in the nominally sinusoidal wave that is due to the geometry of the magnetic field, but it is of little consequence.

Deflection Control at the Overtone

A high pass filter in the positive feedback loop selects the overtone from the X sense signal (at the top right of the circuit diagram). Otherwise the fiber could start up at the fundamental at about 200 Hz. The signal path continues through the overtone select filter, via an all-pass phase shifter to a limiter. This limiter provides the non-linearity (needed in a positive feedback oscillator) to control amplitude. Above a certain fiber deflection amplitude, the limiter produces a signal limited to the supply rails. This constant amplitude signal is then attenuated appropriately at the input to the drive stage to give the desired scan. The drive waveform is therefore not strictly sinusoid but rather square owing to the limiter, which assists in adjusting the X sense signal to be free of contamination from the drive signal. If the drive signal were a sine wave the contamination would be less obvious. With a square wave drive, the compensation can be adjusted to eliminate the square wave addition to the X sense using an oscilloscope.

The role of scan amplitude control can be readily understood if ones imagines switching the system on with that control initially set to zero. If the gain is gradually increased, oscillation will start, producing a low level sine wave when the loop gain is unity. At this point the amplitude rises and falls markedly with the slightest change in the gain control with very slight amplitude regulation occurring with the build up of wind resistance and other level dependent losses. Advancing the control further will increase the amplitude at the limiter input so that clipping of the upper and lower peaks of the sine wave starts. At sufficiently high amplitude, the waveform at the input to the drive stage will approach the square wave referred to above.

Suppression of Vibration at the Fundamental

Some of the characteristics of the negative feedback loop used for vibration damping contrast sharply with the positive loop described above. For example, it aims to provide maximum possible loop gain, provide linearity, and emphasise the lower frequency region (particularly the fundamental mechanical resonance), without disturbing the oscillating loop but while maintaining a phase margin over the entire frequency range. The intended negative loop could easily turn positive outside the frequency range of interest.

It might be imagined that a single loop would suffice, with the phase characteristic adjusted over the two frequency ranges to act as a negative loop at low frequencies and a positive loop at high frequencies. However, the non-linearity needed for amplitude control would cause cross-modulation of the signals in the drive to the X drive coil 56a. For that reason parallel loops are employed in this embodiment, which add after the limiter at the input to the drive stage.

Thus, commencing at the X sense signal, a peaked low pass filter selects the fundamental frequency range in a negative loop that has direct access to the drive stage, effectively bypassing the limiter used for amplitude control of the overtone. During scanning the loop gain can be adjusted for best results in terms of the interference to the image from external vibration. Alternatively the loop gain can be quantified by inserting a low amplitude probe signal into the drive stage and observing the signal returned at the filter output, which has passed through the entire system of X coils 56a, 56b and fiber 42. As the probe signal is tuned through the resonance band, amplitude and phase is measured relative to the probe. If the phase difference is close to 180° at peak response, the loop can be safely closed and vibration damping can be demonstrated.

Provision of Synchronising Signal for Imaging

A distinction should be drawn between scanning versus imaging from a scan. Further, scanner 40 separately provides synchronising for image creation independent of excitation or return light being emitted by, or reflected back into, the fiber 42. In applications such as bar code scanning all required information can be picked up from the target, but for reliable endoscope imaging it is necessary to know the location of the tip of fiber 42 so that an image can be generated.

A virtue of confocal microscopy is that out-of-focus light is not admitted to the image. Operators often find that, on starting up a confocal microscope, the entire field of view is dark because the focal surface does not happen to intersect the object under view. Only as the depth is scanned (in the z direction) does any image information appear. For these reasons image-independent synchronising is essential for confocal microscopy.

Thus, returning to the top right of FIG. 8, the X sense signal is processed for zero crossing (centre of display) and the imaging equipment can display the scanned signal using appropriate delay.

At the start-up of the scanner 40 and its electronics, this X synchronising signal initiates the whole computer loop that provides the Y scan signal back to the scanner 40.

Y Electronics

Figure 9:
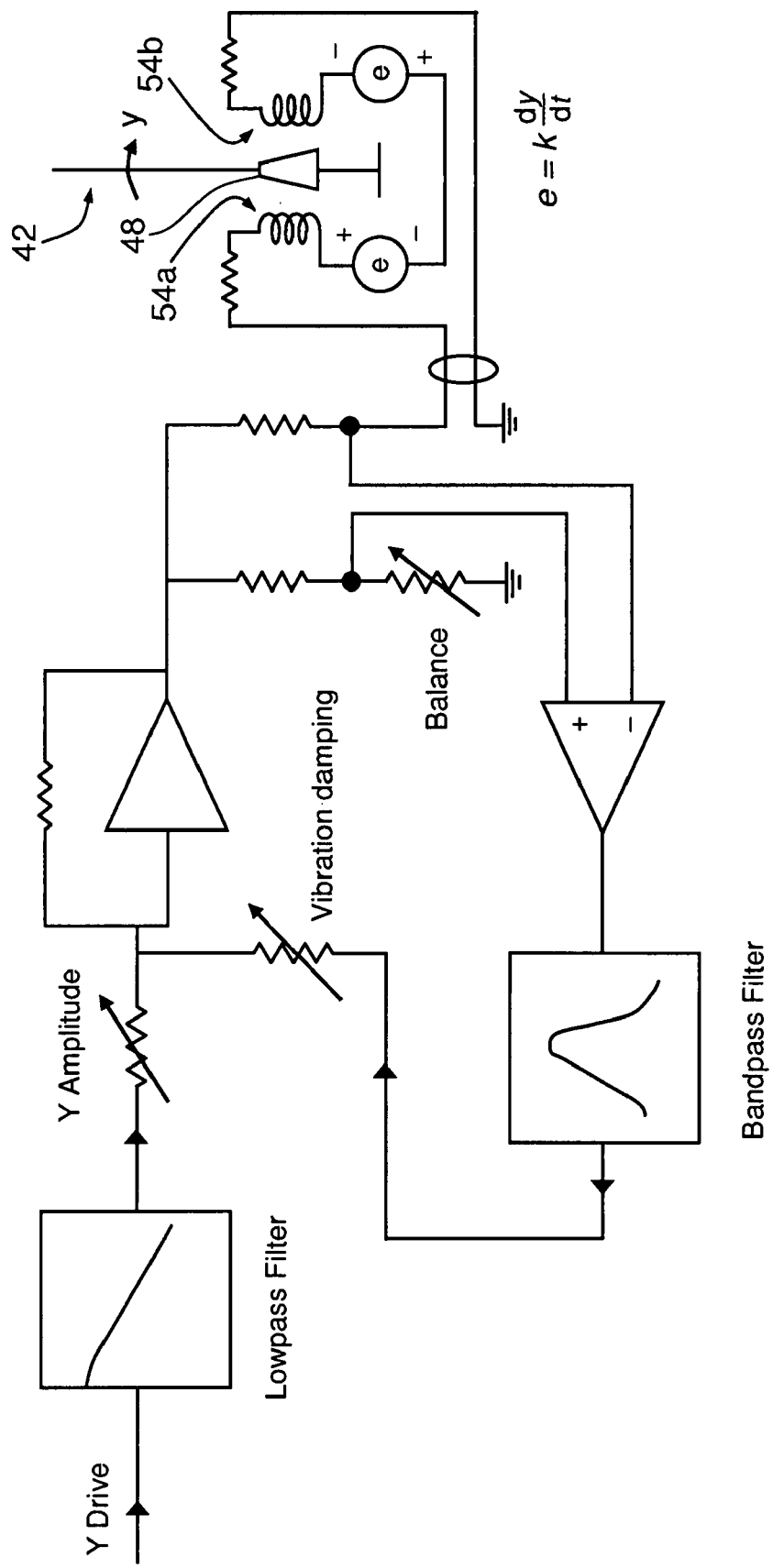
FIG. 9 is a circuit diagram of the Y electronics of the scanner of FIG. 2A.

FIG. 9 is a circuit diagram of the Y electronics of scanner 40, which control the Y drive to move the fiber 42 and magnet 48 in the y direction. Both Y coils 54a, 54b carry drive current, for reasons of symmetry and to obtain adequate deflection of the magnet.

The force in the y direction acting on the magnet 48 has x components that are balanced. With only one Y coil in action, x would be modulated as the y scan proceeded, and at the extremes—where the magnet 48 approaches the poles of the Y coils—there would be the danger of the scan becoming elliptical. In addition, deflection in the y direction would not be as linear in terms of Y current.

There is another symmetry condition related to induction of the X drive field into the Y coils 54a, 54b. The X drive coil 56a is adjacent to, and almost in contact with, both Y coils 54a, 54b (as shown in FIG. 3). By connecting Y coils 54a, 54b in series as shown in FIG. 9, the induction of X into Y is largely cancelled.

The Y drive signal enters the Y electronics (from imaging equipment) at the upper left of FIG. 9; this signal is typically derived from a digital to analogue converter, and it is important to remove any components near the fundamental frequency. These can come from both the conversion and any sharp flyback of the sawtooth. Both are attenuated by a filter designed for a time domain response with no overshoot or ringing even for instantaneous retrace.

There remains the problem of ringing at the fundamental due to vibration in the external environment. Since there is no Y sense coil, the emf induced in the Y coils 54a, 54b by the movement of the magnet 48 is used. This is done in the presence of the sawtooth drive in both Y coils.

A bridge is provided (to the left of the Y coils in the figure), which is used to cancel the drive signal and extract the voltage induced in both coils by magnet vibration in the y direction. The bridge output is amplified and passed through a bandpass filter, and added to the Y drive to quench the fundamental resonance in the Y direction.

Testing

In addition to the potential perturbing effects discussed above, simple vibrational interference to the scan and the more subtle parametric modulation effect (where amplitude depends on mounting compliance) can present problems. The former arises from movement of the scanner during use (such as in an endoscope in vivo).

One may consider how the bending moment for scanning is supplied at the base of the cantilever fiber 42. The large moment required for the tine of a tuning fork scanner can only be provided by a balancing, preferably thicker, tine. By eliminating the fork entirely, the bending moment is reduced by an order of magnitude for a given deflection, as is the drive force also, and most importantly, the mechanical Q. The scanner 40 is thus less sensitive to mounting factors.

EXAMPLES

An X-only fiber cantilever was tested with a light weight mounting. The X sense signal was then measured under a variety of mounting conditions with constant drive. The amplitude varied by only a few percent, except for one case where clamping with pliers some distance from the base seemed to resonate together with the assembly. Merely touching the fiber mount region made the effect disappear.

Two scanners were then constructed, based on scanner 40, and incorporated into an endoscope. Several images were taken with these two scanners. FIG. 10A is an image (reproduced in negative in FIG. 10B for clarity) of fluorescent fibers collected with the first of these scanners, and shows the effect of interference from vibration at the fundamental mechanical resonance. Although it appears as jitter in the x direction, it comes from very small glitches in the Y drive waveform. Similar effects could be produced with rapid retrace in the absence of careful filtering of the Y drive.

FIG. 11 is an image of woven fibers collected with the second scanner, in which the jitter is absent in both X or Y directions and individual fibers can be seen showing fine detail.

Figure 12:
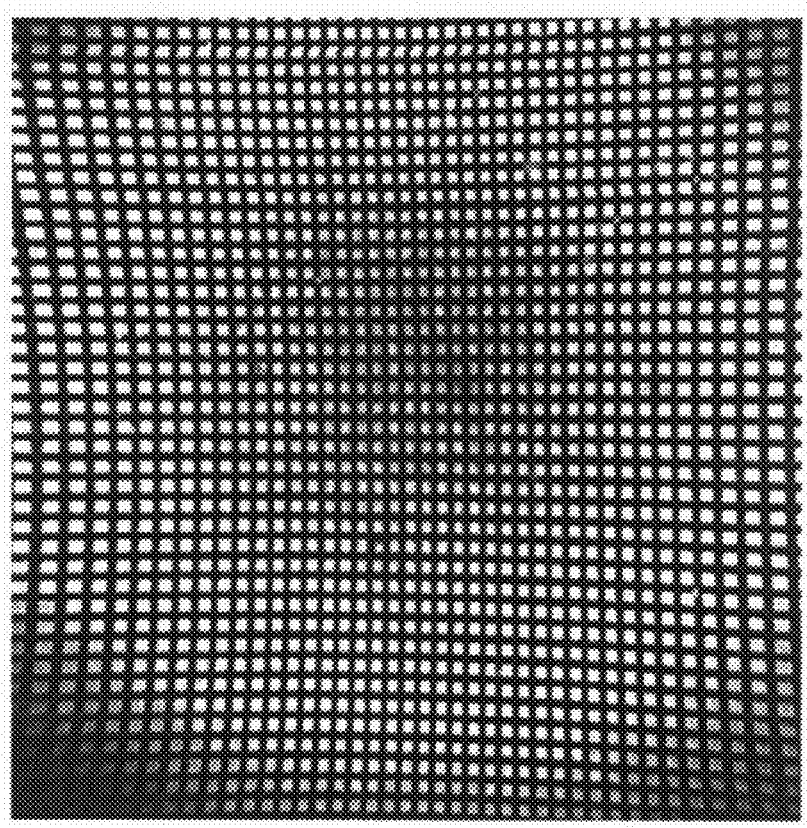
FIG. 12 is an exemplary image of a fluorescent grid collected with the endoscope used to collect the image of FIG. 11.

FIG. 12 is an image of a demanding target comprising a fluorescent grid at 12.5 micron spacing, and collected with the same scanner used to collect the image of FIG. 11. This gives an indication of the field of view and linearity that can be achieved. The image has an approximately uniform scale over the entire field of view.

Figure 2C:
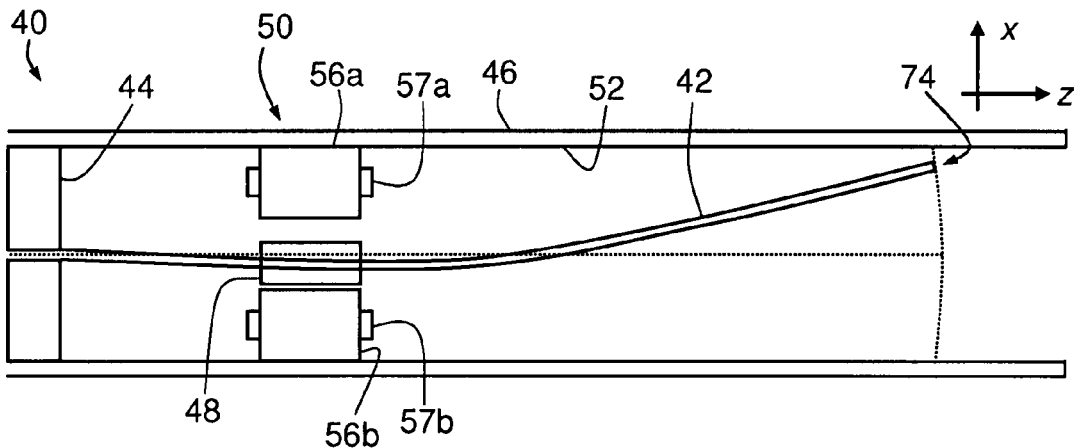
FIG. 2C is another schematic side view of the scanner of FIG. 2A in use.
Figure 13A:
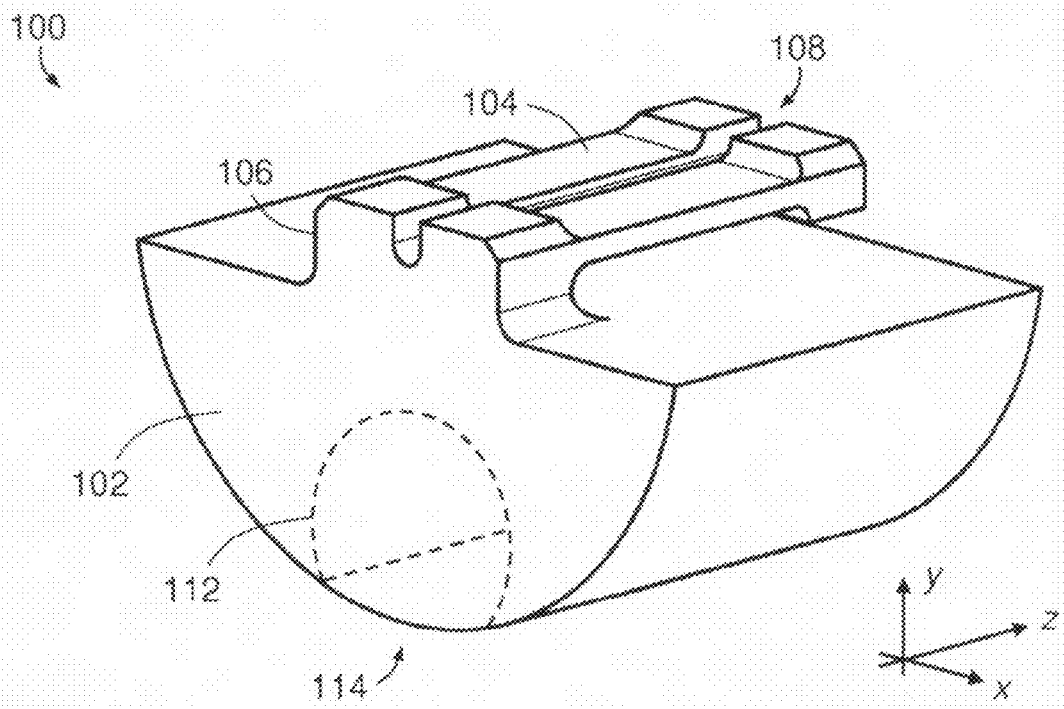
FIGS. 13A, 13B and 13C are views of an alternative fiber mount according to an embodiment of the present invention for use with the scanner of FIG. 2A.
Figure 13B:
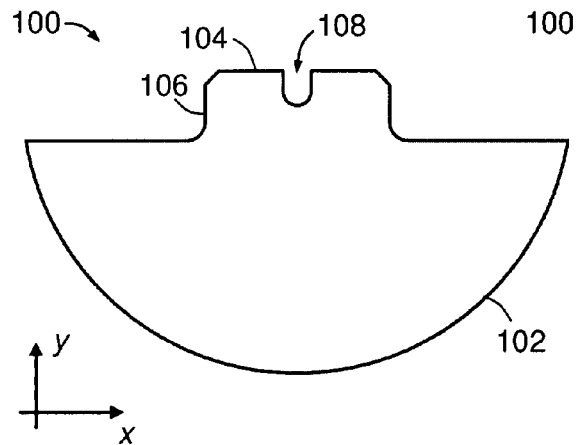
Figure 13C:
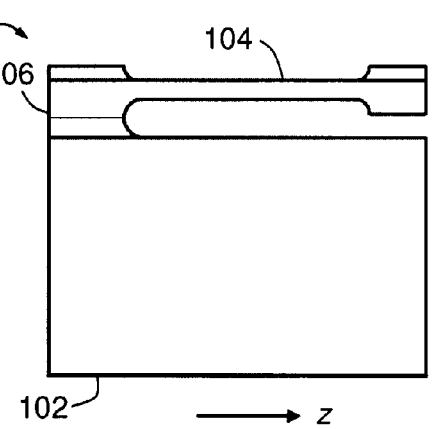

FIGS. 13A, 13B and 13C are views of an alternative fiber mount 100 (viz. alternative to mount 44), according to an embodiment of the present invention, for use with the scanner 40 of FIG. 2A. Fiber mount 100—of wire cut titanium—comprises a generally semi-cylindrical base 102 (for locating in cylindrical housing 46 of scanner 40) and an integral forwardly directed cantilever 104 for holding an optical fiber 42, and joined to base 102 by neck 106. Base 102 has a diameter of approximately 3 mm. Cantilever 104 includes a upper groove 108 for receiving a portion of fiber 42, which then projects forwardly (i.e. in z direction) beyond cantilever 104 so that its forward end can be scanned essentially as illustrated in FIGS. 2A to 2C. Base 102 is formed as less than a complete semi-cylinder to thereby locate groove 108 such that fiber 42 is coaxial with cylindrical housing 46. Fiber 42 is held in groove 108 with an adhesive. Groove 108 is longer (in the z direction) than the thickness (in the z direction) of mount 44, so fiber 42 can be more securely located in fiber mount 100 of this embodiment than in mount 44.

In addition, cantilever 104 acts somewhat like a springboard as it has a width in the lateral or x direction (of approximately 1 mm) that is significantly greater than its thickness in the vertical or y direction; it is thus stiffer and hence more resistant to displacement in the x direction than in the y direction. As a result, in an embodiment of scanner 40 with fiber mount 100, the resonance frequency for vibration of fiber 42 in the x direction was found to be 46 kHz greater than the resonance frequency for vibration of fiber 42 in the y direction, thereby facilitating a fast X scan and a slow Y scan.

Fiber mount 100 may optically include a generally cylindrical cut-out 112 in its lower periphery 114, to lighten mount 100 or to provide a feed-through to the forward portion of scanner 40 for electrical cables or the like.

Figure 14A:
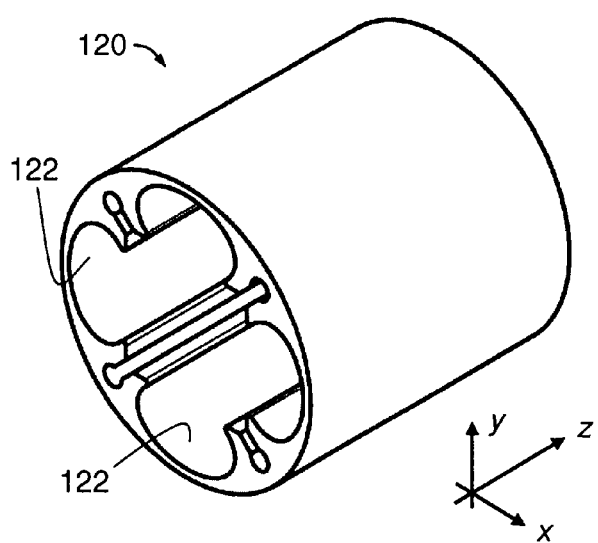
FIGS. 14A, 14B and 14C are views of an alternative coil holder according to an embodiment of the present invention for use with the scanner of FIG. 2A.
Figure 14B:
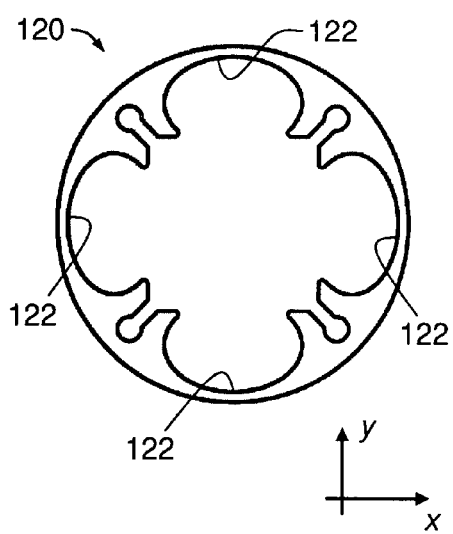
Figure 14C:
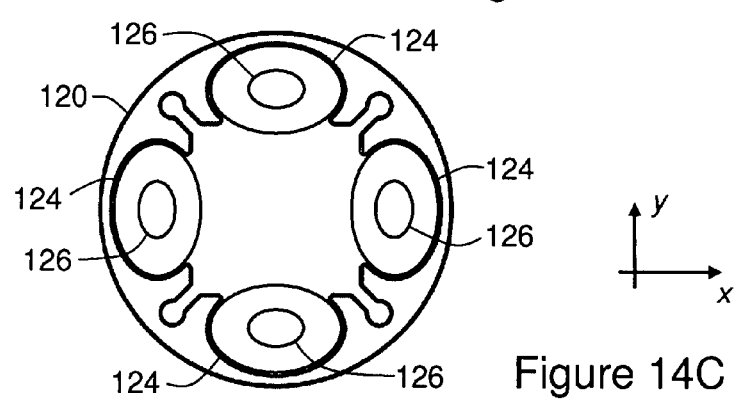

FIGS. 14A, 14B and 14C are views of an alternative coil holder 120, according to an embodiment of the present invention, for use with the scanner 40 of FIG. 2A. FIG. 14C depicts coil holder 120 provided with coils. Coil holder 120—also of wire cut titanium—is generally cylindrical with a diameter of approximately 3 mm, and includes four identical and evenly spaced elliptical internal recesses 122 for accommodating four elliptical electromagnetic coils (shown at 124 in FIG. 14C) comparable to coils 50 of scanner 40. Unlike coils 50 of scanner 40, however, coils 124 are held by their outer windings rather than by their cores 126, through the engagement of their outer windings and the surfaces of respective recesses 122. Hence, coils 124 do not abut the interior wall of cylindrical housing 46, but rather abut the surfaces of recesses 122. Coil holder 120 allows precise and quick positioning of coils 124, and is inexpensive to manufacture.

In addition, one or more slots or grooves (not shown) may optionally be provided in the external surface of coil holder 120 for engaging corresponding flanges provided on interior wall 52 of housing 46. These optional grooves and flanges would facilitate the positioning and securing in position of coil holder 120.

Figure 15:
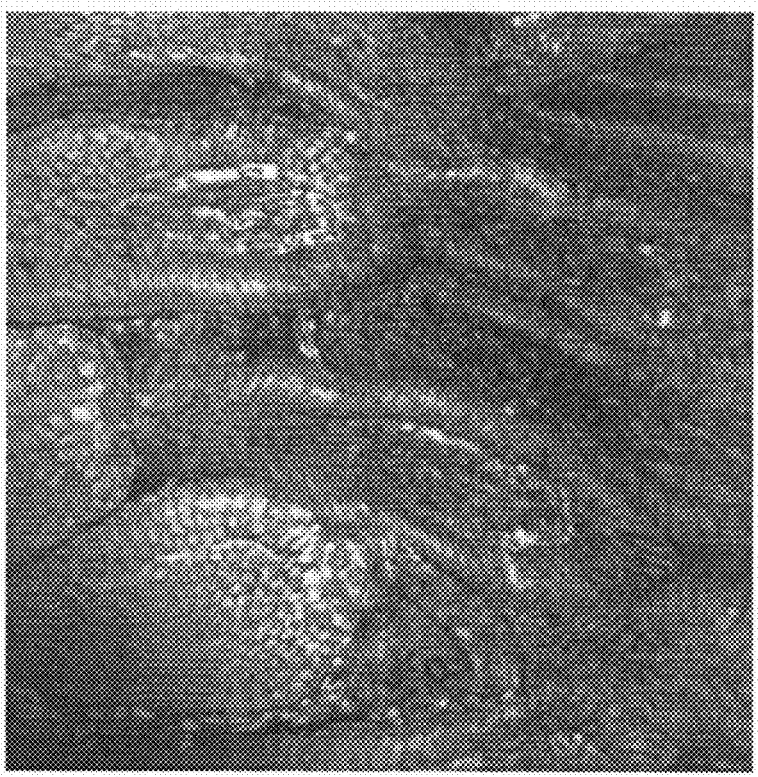
FIG. 15 is an image of small intestine villi from a mouse obtained with the scanner of FIG. 2A employing the fiber mount of FIGS. 13A to 13C and the coil holder of FIGS. 14A, 14B and 14C.

FIG. 15 is an image of small intestine villi from a mouse, obtained with a confocal endoscope comprising an optical fiber scanner according to the embodiment of FIG. 2A though employing fiber mount 100 of FIGS. 13A to 13C and coil holder 120 of FIGS. 14A and 14B. The mouse was intravenously injected with 0.5 mL of a 1% solution of sodium fluorescein, and topical acriflavine (0.05% solution) was applied to the villi; the tissue was then imaged using 488 nm laser illumination.

Figure 16:
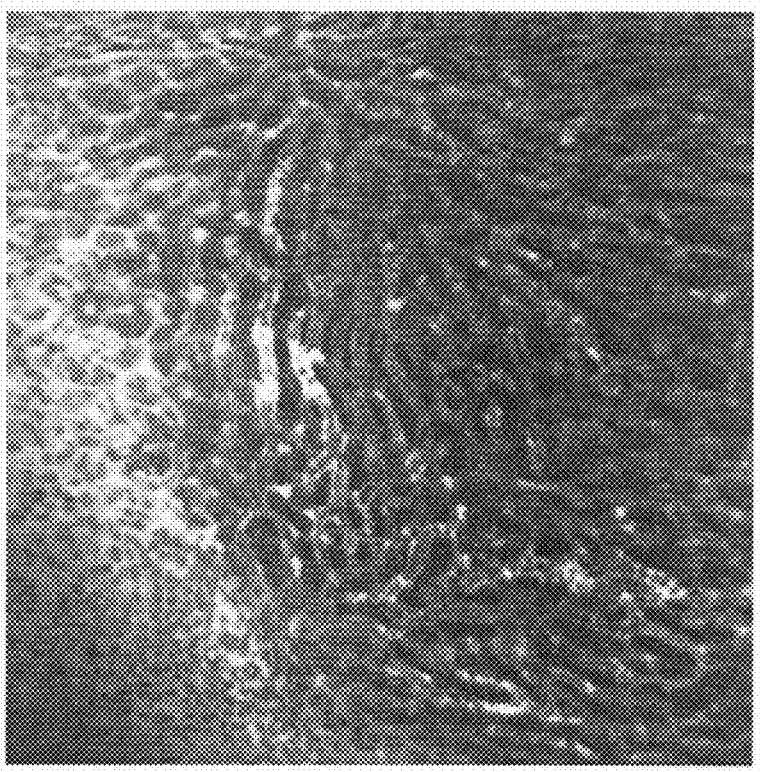
FIG. 16 is an image of liver vessels from a mouse obtained with the scanner of FIG. 2A employing the fiber mount of FIGS. 13A to 13C and the coil holder of FIGS. 14A, 14B and 14C.

FIG. 16 is an image of liver vessels from a mouse, collected with the same apparatus as was the image of FIG. 15. The sample was prepared in the same manner as was that imaged in FIG. 15 (though without the application of topical acriflavine).

The field of view is approximately 500 μm×500 μm for the images of both FIGS. 15 and 16.

In one embodiment, the invention provides a method of scanning with a light transmitter having an exit tip. The method comprises supporting said light transmitter in a mount located remotely from said exit tip, applying a driving force to said light transmitter between said mount and said exit tip, driving said light transmitter to vibrate resonantly in a first direction with a first driving force and to vibrate non-resonantly in a second direction orthogonal to said first direction with a second driving force, and synchronizing vibration of said light transmitter in said first direction with vibration of said light transmitter in said second direction so that the exit tip of the light transmitter executes a scan pattern. The method may further comprise driving said light transmitter with an axially polarised magnet mounted on said light transmitter, wherein a first pair of axially oriented electromagnetic coils are located on either side of the magnet in the first direction, the first pair of coils comprising a drive coil for driving said magnet in said first direction and a sensor coil for providing a signal for use in generating a position signal indicative of the position of the magnet in the first direction, and a second pair of axially oriented electromagnetic coils are located on either side of the magnet in said second direction for driving the magnet in the second direction, and using said position signal to provide positive feedback to maintain light transmitter vibration in said first direction. The method may further comprise vibrating said light transmitter in said second direction non-resonantly with low frequency alternating current excitation of said second pair of coils. The method may further comprise vibrating said light transmitter in said second direction non-resonantly with varying direct current excitation of said second pair of coils. The method may further comprise providing a restorative force with a spring or with a resilience of said light transmitter.

In another embodiment, the invention provides a scanning apparatus. The scanning apparatus comprises a light transmitter having an exit tip, a mount configured to support said light transmitter and located remotely from said exit tip, a drive configured to drive said light transmitter to vibrate resonantly in a first direction with a first driving force and to vibrate non-resonantly in a second direction orthogonal to said first direction with a second driving force, and a synchronizer configured to synchronize vibration of said light transmitter in said first direction with vibration of said light transmitter in said second direction so that said exit tip of said light transmitter executes a scan pattern, where said drive applies a driving force to said light transmitter between said mount and said exit tip. The apparatus may further comprise an axially polarised magnet mounted on said light transmitter, a first pair of axially oriented electromagnetic coils located on either side of said magnet in said first direction comprising, the first pair of coils comprising a drive coil configured to drive said magnet in said first direction and a sensor coil configured to provide a signal for use in generating a position signal indicative of the position of said magnet in said first direction, and a second pair of axially oriented electromagnetic coils located on either side of said magnet in said second direction configured to drive said magnet in said second direction, where said position signal is suitable for providing feedback to maintain light transmitter vibration in said first direction. The apparatus may be further configured to subtract a signal proportional to a drive current from said position signal to compensate for contamination of said position signal by a current induced in said sensor coil by the magnetic field of said drive coil. The apparatus may be included in an imaging device, an endoscope, an endomicroscope, an optical coherence tomograph, a confocal microscope, a confocal endoscope or a confocal multiphoton endoscope.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention. Further, any reference herein to prior art is not intended to imply that such prior art forms or formed a part of the common general knowledge.

What is claimed:

1. A method of scanning with a light transmitter having an exit tip, comprising:
  supporting said light transmitter in a mount located remotely from said exit tip;
  applying a first driving force to said light transmitter between said mount and said exit tip to resonantly vibrate said light transmitter in a first direction; and
  applying a second driving force to said light transmitter between said mount and said exit tip to non-resonantly vibrate said light transmitter in a second direction orthogonal to said first direction, wherein vibration of said light transmitter in said first direction and vibration of said light transmitter in said second direction are synchronized so that the exit tip of the light transmitter executes a scan pattern, wherein said scan pattern approximates a rectilinear raster scan and said light transmitter executes a sinusoidal vibration in said first direction and a linear vibration in said second direction.

2. The method as claimed in claim 1, wherein applying said first driving force comprises vibrating said light transmitter in said first direction at the first overtone of mechanical resonance.

3. The method as claimed in claim 1, wherein driving said light transmitter comprises:
driving said light transmitter with an axially polarized magnet mounted on said light transmitter, wherein a first pair of axially oriented electromagnetic coils are located on either side of the magnet in the first direction, the first pair of coils comprising a drive coil for driving said magnet in said first direction and a sensor coil for providing a signal for use in generating a position signal indicative of the position of the magnet in the first direction, and a second pair of axially oriented electromagnetic coils are located on either side of the magnet in said second direction for driving the magnet in the second direction; and the method further comprises:
using said position signal to provide positive feedback to maintain light transmitter vibration in said first direction.

4. The method as claimed in claim 3, further comprising using said position signal for synchronizing an image display.

5. The method as claimed in claim 3, further comprising deriving said position signal by integrating said output signal of said sensor coil.

6. The method as claimed in claim 3, further comprising driving said drive coil with a drive current and subtracting a signal proportional to said drive current from said position signal to compensate for contamination of said position signal by a current induced in said sensor coil by the magnetic field of said drive coil.

7. The method as claimed in claim 3, wherein driving said light transmitter further comprises employing additional coils for driving said light transmitter in one or both of said first direction and said second direction.

8. The method as claimed in claim 3, further comprising locating said magnet substantially at a vibration antinode so that said magnet moves laterally without significant rotation, or substantially at a minimum in the overtone frequency versus magnet position curve to minimize required light transmitter length.

9. The method as claimed in claim 3, further comprising locating said magnet substantially at both a vibration antinode and a minimum in the overtone frequency versus magnet position curve.

10. The method as claimed in claim 1, wherein said light transmitter comprises an optical fiber or a plurality of optical fibers or an optical fiber bundle.

11. The method as claimed in claim 1, further comprising providing negative feedback at a fundamental frequency in both said first and second directions.

12. The method as claimed in claim 1, further comprising mounting said light transmitter to have compliance in said first direction that is significantly different from compliance in said second direction.

13. The method as claimed in claim 1, further comprising mounting said light transmitter on a thin transverse beam.

14. The method as claimed in claim 1, further comprising mounting said light transmitter on a cantilever with a lower resonant frequency in one of said first and second directions than in the other of said first and second directions.

15. A scanning apparatus, comprising:
a light transmitter having an exit tip;
a mount configured to support said light transmitter and located remotely from said exit tip; and
a drive circuit configured to apply a first driving force to said light transmitter between said mount and said exit tip to resonantly vibrate said light transmitter in a first direction and to apply a second driving force to said light transmitter between said mount and said exit tip to non-resonantly vibrate said light transmitter in a second direction orthogonal to said first direction, wherein vibration of said light transmitter in said first direction and vibration of said light transmitter in said second direction are synchronized so that the exit tip of the light transmitter executes a scan pattern, wherein said scan pattern approximates a rectilinear raster scan and said light transmitter executes a sinusoidal vibration in said first direction and a linear vibration in said second direction.

16. The apparatus as claimed in claim 15, wherein the drive comprises:
an axially polarized magnet mounted on said light transmitter;
a first pair of axially oriented electromagnetic coils located on either side of said magnet in said first direction comprising, the first pair of coils comprising a drive coil configured to drive said magnet in said first direction and a sensor coil configured to provide a signal for use in generating a position signal indicative of the position of said magnet in said first direction; and
a second pair of axially oriented electromagnetic coils located on either side of said magnet in said second direction configured to drive said magnet in said second direction;
wherein said position signal is suitable for providing feedback to maintain light transmitter vibration in said first direction.

17. The apparatus as claimed in claim 16, further comprising an integrator configured to integrate an output signal of said sensor coil to generate said position signal.

18. The apparatus as claimed in claim 16, wherein said magnet is located substantially at a vibration antinode so that said magnet moves laterally without significant rotation, or substantially at a minimum in the overtone frequency versus magnet position curve, or substantially at both a vibration antinode and a minimum in said overtone frequency versus magnet position curve.

19. The apparatus as claimed in claim 16, wherein the drive is further configured to vibrate said light transmitter in said second direction non-resonantly with low frequency alternating current excitation of said second pair of coils.

20. The apparatus as claimed in claim 16, further comprising a source of varying direct current configured to excite said second pair of coils and thereby vibrate said light transmitter in said second direction non-resonantly.

21. The apparatus as claimed in claim 15, further comprising a spring or other resilient mechanism configured to provide a restorative force to said light transmitter.

22. The apparatus as claimed in claim 15, wherein said mount has significantly different compliances in said first and second directions.

23. The apparatus as claimed in claim 15, comprising an imaging system configured to process return light from said light transmitter and displaying an image generated therefrom.

24. The apparatus as claimed in claim 15, wherein said apparatus has a diameter of approximately 3.0 to 4.5 mm and a length of approximately 23 to 30 mm.

* * * * *